United States Patent
Kawamura et al.

(10) Patent No.: US 8,951,739 B2
(45) Date of Patent: Feb. 10, 2015

(54) BIOMARKER FOR DEPRESSION, METHOD FOR MEASURING A BIOMARKER FOR DEPRESSION, COMPUTER PROGRAM, AND RECORDING MEDIUM

(75) Inventors: Noriyuki Kawamura, Tokyo (JP); Kosaku Shinoda, Yamagata (JP); Yoshiaki Ohashi, Yamagata (JP); Takamasa Ishikawa, Yamagata (JP); Hajime Sato, Yamagata (JP)

(73) Assignee: Human Metabolome Technologies Inc., Yamagata (JP)

( * ) Notice: Subject to any disclaimer, the term of this patent is extended or adjusted under 35 U.S.C. 154(b) by 33 days.

(21) Appl. No.: 13/389,903

(22) PCT Filed: Aug. 12, 2010

(86) PCT No.: PCT/JP2010/063713
§ 371 (c)(1),
(2), (4) Date: Jun. 27, 2012

(87) PCT Pub. No.: WO2011/019072
PCT Pub. Date: Feb. 17, 2011

(65) Prior Publication Data
US 2012/0282592 A1    Nov. 8, 2012

(30) Foreign Application Priority Data
Aug. 12, 2009 (JP) .................. 2009-187521
Dec. 22, 2009 (JP) .................. 2009-291029

(51) Int. Cl.
*G01N 33/53* (2006.01)
*G01N 33/68* (2006.01)

(52) U.S. Cl.
CPC ...... *G01N 33/6893* (2013.01); *G01N 2800/304* (2013.01)
USPC .......................................... 435/7.1; 436/518

(58) Field of Classification Search
None
See application file for complete search history.

(56) References Cited

U.S. PATENT DOCUMENTS

2007/0173901 A1    7/2007 Reeve

FOREIGN PATENT DOCUMENTS

JP    2009-524450    7/2009
WO   WO2009006338   1/2009

OTHER PUBLICATIONS

Modica-Napolitano et al. Biol Psychiatry 2004 vol. 55, 273-277.*
PCT Search Report for PCT/JP2010/063713, completed Jan. 11, 2011.
Enokido, Yasushi, et al., Cystathionine Beta-Synthase, A Key Enzyme for Homocysteine Metabolism, Is Preferentially Expressed in the Radial Glia/Astrocyte Linage of Developing Mouse CNS; 2005; The FSAB Journal; vol. 19; pp. 1854-1856.
Bertolini A.M. et al., "Deficiency of amino acids as precursors of chemical mediators and creatine in older people," *Minerva Medica*, 1981; 72: 2157-2160 (foreign language).
Bertolini A.M. et al., "Deficiency of amino acids as precursors of chemical mediators and creatine in older people," *Minerva Medica*, 1981; 72: 2157-2160 (English translation).
Human Matabolome Databases version 3.5, showing metabocard for O-Phosphoethanolamine (HMDB00224), Normal Concentrations, http://www.hmdb.ca/metabolites/HMDB00224, downloaded Feb. 2014.
Eastman J.R. et al., Urinary phosphoethanolamine: Normal Values by age, Clinical Chemistry vol. 26, No. 12, 1980, pp. 1757-1758.
Perry et al., Technical pitfalls leading to errors in the quantitation of plasma amino acids, Clin. Chim. Acta 25, 1969, pp. 53-58.
Ghadimi et al., Free amino acids of cord plasma as compared with material plasma during pregnancy, Pediatrics Official Journal of the American Academy of Pediatrics, Print ISSN 0031-4005, 1964, pp. 500-502.

* cited by examiner

*Primary Examiner* — Jacob Cheu
(74) *Attorney, Agent, or Firm* — Edell, Shapiro & Finnan, LLC

(57) ABSTRACT

Provided is a method for using low molecular weight compounds found in the body as a biomarker for diagnosing depression. Specifically, more than one compound selected from a group comprising the following are used: ADP-ribose, ATP, ADP, AMP, serotonin, tryptophan, kynurenine, SDMA (symmetrical dimethylarginine), threonine, glyceric acid, serine, N-acetylaspartic acid, glutamic acid, trigonelline, creatine, 2-methylserine, sphingosine, homovanillic acid, piperidine, sulfoxidized methionine, pipecolic acid, sphinganine, gamma-butyrobetaine, guanidinoacetic acid, isobutyric acid, creatinine, sarcosine, 3-methylbutyric acid, nicotinamide, betaine, ornithine, carnitine, ethanolamine, phosphoethanolamine, taurine, hypotaurine, aspartic acid, methionine, and tyrosine.

12 Claims, No Drawings

BIOMARKER FOR DEPRESSION, METHOD FOR MEASURING A BIOMARKER FOR DEPRESSION, COMPUTER PROGRAM, AND RECORDING MEDIUM

CROSS-REFERENCE TO RELATED APPLICATIONS

This application is a U.S. national counterpart application of PCT International Application Serial No. PCT/JP2010/063713, filed Aug. 12, 2010, which claims priority to Japanese Patent Application Serial No. 2009-187521 having a filing date of 12 Aug. 2009 and Japanese Patent Application Serial No. 2009-291029 having a filing date of 22 Dec. 2009, all of which are incorporated herein in their entireties by this reference.

TECHNICAL FIELD

The present invention relates to biomarkers for diagnosing depression.

BACKGROUND ART

The depression is one type of mood disorders, and its predominant symptoms are the "depressed mood" and "loss of interest or pleasure", but some patients complain other symptoms such as suppressed appetite, insomnia, fatigue, suicidal ideation etc. Its diagnosis is generally conducted based on the criterion under either ICD-10 (International Classification of Diseases) by WHO (World Health Organization) or "DSM-IV" by American Psychiatric Association.

However, the diagnosis of depression can be hardly objective because it depends on the impression by physician or psychologists, or impression by the patients or individuals complaining the symptom or stress. In fact, cases are often observed where symptoms are excessively reported either intentionally or unintentionally because of the disease gain in which a patient is somehow benefitted from the state of being sick, or otherwise symptoms are concealed for the purpose of avoiding prejudice or trouble from being known to be in depression. In such cases, accurate diagnosis of the disease is difficult, and determination of treatment method may become difficult, or even inappropriate treatment might be applied due to misdiagnosis.

Therefore, several methods have been tested to objectively assist the diagnosis by physician or psychologists. One example is the method in which the noise appearing in the symptom of a patient is excluded as much as possible by processing the results of diagnosis made by a physician or psychologist with a computer (WO2004/080312).

Several markers for depression are known, including macromolecular materials which have been reported in the method to measure the expression level of a gene (JP2008-253258) and the method to detect proteolytic products (JP2009-92550).

On the other hand, smaller compounds in living bodies are also tested as candidates for the depression marker, including those having been reported in the method to measure and analyze the contents of testosterone and cortisol (JP2007-24822) and the method to detect the degraded products of tryptophan in vivo (WO2006/105907), but none of them is brought into practice use so far.

SUMMARY OF INVENTION

Technical Problem

The present invention is aimed to provide biomarkers for diagnosing depression.

Solution to Problem

The present invention consists of the following Items.

(1) A biomarker for diagnosing depression, wherein the biomarker is selected from the group consisting of ADP-RIBOSE, ATP, ADP, AMP, serotonin, tryptophan, kynurenine, SDMA (symmetric dimethylarginine), threonine, glyceric acid, serine, N-acetylaspartic acid, glutamic acid, trigonelline, creatine, 2-methyl serine, sphingosine, homovanillic acid, piperidine, sulfoxidated methionine, pipecolic acid, sphinganine, γ-butyrobetaine, guanidoacetic acid, isobutyric acid, creatinine, sarcosine, 3-methyl butyric acid, nicotinamide, betaine, ornithine, carnitine, ethanolamine, phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA (asymmetric dimethylarginine), isoleucine, hydroxyproline and cystathionine.

(2) The biomarker for diagnosing depression according to Item (1), wherein the biomarker is selected from the group consisting of phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA, isoleucine, hydroxyproline and cystathionine.

(3) The biomarker for diagnosing depression according to Item (1), wherein the biomarker is selected from the group consisting of phosphoethanolamine, taurine, aspartic acid, methionine, tyrosine, aminoadipic acid, histidine and isoleucine.

(4) The biomarker for diagnosing depression according to Item (1), wherein the biomarker is selected from the group consisting of hypotaurine, phosphorylcholine, arginine, 3-aminobutyric acid, β-alanine, lysine, phosphocreatine, alanine, uric acid, choline, isocitric acid, leucine, malic acid, tyramine, valine and ADMA.

(5) The biomarker for diagnosing depression according to Item (1), wherein the biomarker is selected from the group consisting of asparagine, phenylalanine, glucaric acid, hydroxyproline and cystathionine.

(6) The biomarker for diagnosing depression according to Item (1), wherein the biomarker is cystathionine.

(7) The biomarker for diagnosing depression according to Item (1), wherein the biomarker is selected from the group consisting of ADMA, hypotaurine, lysine, histidine, leucine, β-alanine, choline, threonine, glyceric acid, isocitric acid, serine, malic acid, 2-methyl serine, sphingosine, homovanillic acid, sulfoxidated methionine, sphinganine, phenylalanine, alanine, 2-aminoadipic acid, N-acetylaspartic acid, glutamic acid, trigonelline, creatine, guanidoacetic acid, isobutyric acid, creatinine, sarcosine, betaine, phosphoethanolamine, taurine, ADP-RIBOSE, aspartic acid, tyrosine, ATP, ADP, asparagine, AMP, serotonin, valine, tryptophan, kynurenine, phosphorylcholine, isoleucine, SDMA, piperidine, pipecolic acid, creatine, nicotinamide, γ-butyrobetaine, uric acid, 3-methyl butyric acid, 3-aminobutyric acid, ornithine, carnitine, ethanolamine and methionine.

(8) The biomarker for diagnosing depression according to Item (1), wherein the biomarker is selected from the group consisting of methionine, phosphoethanolamine, taurine, ADP-RIBOSE, aspartic acid, tyrosine, ATP, ADP, asparagine, AMP, serotonin, valine, tryptophan, kynurenine, phosphorylcholine, isoleucine, SDMA, piperidine, pipecolic acid, creatinine and nicotinamide.

(9) The biomarker for diagnosing depression according to Item (1), wherein the biomarker is selected from the group consisting of ADMA, hypotaurine, lysine, histidine, leucine, β-alanine, choline, threonine, glyceric acid, isocitric acid, serine, malic acid, 2-methyl serine, sphingosine, homovanillic acid, sulfoxidated methionine, sphinganine, isobutyric acid, γ-butyrobetaine, uric acid, 3-methyl butyric acid, 3-aminobutyric acid, ornithine, carnitine and ethanolamine.

(10) The biomarker for diagnosing depression according to Item (1), wherein the biomarker is selected from the group consisting of phenylalanine, alanine, aminoadipic acid, N-acetylaspartic acid, glutamic acid, trigonelline, creatine, guanidoacetic acid, sarcosine and betaine.

(11) A method of measurement including the step of measuring a content of one or more compounds selected from the group consisting of ADP-RIBOSE, ATP, ADP, AMP, serotonin, tryptophan, kynurenine, SDMA(symmetric dimethylarginine), threonine, glyceric acid, serine, N-acetylaspartic acid, glutamic acid, trigonelline, creatine, 2-methyl serine, sphingosine, homovanillic acid, piperidine, sulfoxidated methionine, pipecolic acid, sphinganine, γ-butyrobetaine, guanidoacetic acid, isobutyric acid, creatinine, sarcosine, 3-methyl butyric acid, nicotinamide, betaine, ornithine, carnitine, ethanolamine, phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA (asymmetric dimethylarginine), isoleucine, hydroxyproline and cystathionine in a collected blood sample.

(12) The method of measurement according to Item (11), the method including the step of measuring a content of one or more compounds selected from the group consisting of phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA, isoleucine, hydroxyproline and cystathionine in a collected blood sample.

(13) The method of measurement according to Item (11), the method including the steps of:
measuring a content of a first compound selected from the group consisting of hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA, isoleucine, hydroxyproline and cystathionine in a collected blood sample, and measuring a content of a second compound selected from the group consisting of phosphoethanolamine and taurine in the blood sample.

(14) The method of measurement according to Item (11), the method including the step of measuring a content of aspartic acid and arginine in the blood sample.

(15) The method of measurement according to Item (11), the method including the step of measuring a content of aspartic acid and tyrosine in the blood sample.

(16) The method of measurement according to Item (11), the method including the step of measuring a content of tyrosine and glucaric acid in the blood sample.

(17) The method of measurement according to Item (11), the method including the step of measuring a content of tyrosine and 3-aminobutyric acid in the blood sample.

(18) The method of measurement according to Item (11), the method including the step of measuring a content of one or more compounds selected from the group consisting of ADMA, hypotaurine, lysine, histidine, leucine, β-alanine, choline, threonine, glyceric acid, isocitric acid, serine, malic acid, 2-methyl serine, sphingosine, homovanillic acid, sulfoxidated methionine, sphinganine, phenylalanine, alanine, 2-aminoadipic acid, N-acetylaspartic acid, glutamic acid, trigonelline, creatine, guanidoacetic acid, isobutyric acid, creatinine, sarcosine, betaine, phosphoethanolamine, taurine, ADP-RIBOSE, aspartic acid, tyrosine, ATP, ADP, asparagine, AMP, serotonin, valine, tryptophan, kynurenine, phosphorylcholine, isoleucine, SDMA, piperidine, pipecolic acid, creatine, nicotinamide, γ-butyrobetaine, uric acid, 3-methyl butyric acid, 3-aminobutyric acid, ornithine, carnitine, ethanolamine and methionine in a collected blood sample.

(19) A method for judging an effect of a drug for depression, the method including the steps of:
measuring a content of one or more compounds in blood samples collected from a patient afflicted with the depression before and after an administration of the drug to the patient, and
comparing the content of the compound between the blood samples before and after the administration,
wherein the compound is selected from the group consisting of ADP-RIBOSE, pairs of ATP, ADP, AMP, serotonin, tryptophan, kynurenine, SDMA (symmetric dimethylarginine), threonine, glyceric acid, serine, N-acetylaspartic acid, glutamic acid, trigonelline, creatine, 2-methyl serine, sphingosine, homovanillic acid, piperidine, sulfoxidated methionine, pipecolic acid, sphinganine, γ-butyrobetaine, guanidoacetic acid, isobutyric acid, creatinine, sarcosine, 3-methyl butyric acid, nicotinamide, betaine, ornithine, carnitine, ethanolamine, phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA (asymmetric dimethylarginine), isoleucine, hydroxyproline and cystathionine.

(20) The method for judging an effect of a drug for depression according to Item (19), the method including the steps of:
measuring a content of one or more compounds in blood samples collected from a patient afflicted with the depression before and after an administration of the drug to the patient, and
comparing the content of the compound between the blood samples before and after the administration,
wherein the compound is selected from the group consisting of phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA, isoleucine, hydroxyproline and cystathionine.

(21) A method for judging an effect of a drug for a depression, the method including the steps of:
measuring a content of one or more compounds in a blood sample drawn from a patient afflicted with the depression after an administration of the drug to the patient, and
comparing a threshold for a content of the compound in blood to distinguish a patient with depression from a healthy subject with the measured content of the compound,
wherein the compound is selected from the group consisting of ADP-RIBOSE, ATP, ADP, AMP, serotonin, tryptophan, kynurenine, SDMA(symmetric dimethylarginine), threonine, glyceric acid, serine, N-acetylaspartic acid, glutamic acid, trigonelline, creatine, 2-methyl serine, sphingosine, homovanillic acid, piperidine, sulfoxidated methionine, pipecolic acid, sphinganine, γ-butyrobetaine, guanidoacetic acid, isobutyric acid, creatinine, sarcosine, 3-methyl butyric acid, nicotinamide, betaine, ornithine, carnitine, ethanolamine, phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA (asymmetric dimethylarginine), isoleucine, hydroxyproline and cystathionine.

(22) The method for judging an effect of a drug for a depression according to Item (21), the method including the steps of:
measuring a content of one or more compounds in a blood sample drawn from a patient afflicted with the depression after an administration of the drug to the patient, and
comparing a threshold for a content of the compound in blood to distinguish a patient with depression from a healthy subject with the measured content of the compound,
wherein the compound is selected from the group consisting of phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA, isoleucine, hydroxyproline and cystathionine.

(23) A method for determining a threshold for a content of one or more compounds in blood to distinguish a patient with depression from a healthy subject, the method including the step of measuring a content of the compound in blood samples collected from plurality of patients diagnosed as being afflicted with depression and plurality of healthy subjects,
wherein the compound is selected from the group consisting of ADP-RIBOSE, ATP, ADP, AMP, serotonin, tryptophan, kynurenine, SDMA(symmetric dimethylarginine), threonine, glyceric acid, serine, N-acetylaspartic acid, glutamic acid, trigonelline, creatine, 2-methyl serine, sphingosine, homovanillic acid, piperidine, sulfoxidated methionine, pipecolic acid, sphinganine, γ-butyrobetaine, guanidoacetic acid, isobutyric acid, creatinine, sarcosine, 3-methyl butyric acid, nicotinamide, betaine, ornithine, carnitine, ethanolamine, phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA (asymmetric dimethylarginine), isoleucine, hydroxyproline and cystathionine.

(24) The method for determining a threshold of a content of one or more compounds in blood to distinguish a patient with depression from a healthy subject according to Item (23), the method including the step of:
measuring a content of the compound in blood samples collected from plurality of patients diagnosed as being afflicted with depression and plurality of healthy subjects,
wherein the compound is selected from the group consisting of phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA, isoleucine, hydroxyproline and cystathionine.

(25) A method for screening a model animal for depression, the method including the steps of:
collecting a blood sample from a candidate animal, and
measuring a content of one or more compounds selected from the group consisting of ADP-RIBOSE, ATP, ADP, AMP, serotonin, tryptophan, kynurenine, SDMA(symmetric dimethylarginine), threonine, glyceric acid, serine, N-acetylaspartic acid, glutamic acid, trigonelline, creatine, 2-methyl serine, sphingosine, homovanillic acid, piperidine, sulfoxidated methionine, pipecolic acid, sphinganine, γ-butyrobetaine, guanidoacetic acid, isobutyric acid, creatinine, sarcosine, 3-methyl butyric acid, nicotinamide, betaine, ornithine, carnitine, ethanolamine, phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA (asymmetric dimethylarginine), isoleucine, hydroxyproline and cystathionine in the blood sample.

(26) A method for screening a therapeutic agent for patient with depression, the method including the steps of:
administering a candidate substance for the therapeutic agent to a model animal afflicted with the depression,
collecting blood samples before and after the administration of the candidate substance,
measuring a content of one or more compounds in the blood samples, and
comparing the content of the compound between the blood samples before and after the administration of the candidate substance,
wherein the compound is selected from the group consisting of ADP-RIBOSE, ATP, ADP, AMP, serotonin, tryptophan, kynurenine, SDMA(symmetric dimethylarginine), threonine, glyceric acid, serine, N-acetylaspartic acid, glutamic acid, trigonelline, creatine, 2-methyl serine, sphingosine, homovanillic acid, piperidine, sulfoxidated methionine, pipecolic acid, sphinganine, γ-butyrobetaine, guanidoacetic acid, isobutyric acid, creatinine, sarcosine, 3-methyl butyric acid, nicotinamide, betaine, ornithine, carnitine, ethanolamine, phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA (asymmetric dimethylarginine), isoleucine, hydroxyproline and cystathionine.

(27) The method for screening a therapeutic agent for patient with depression according to Item (26), the method including the steps of:

administering a candidate substance for the therapeutic agent to a model animal afflicted with the depression, collecting blood samples before and after the administration of the candidate substance, measuring a content of one or more compounds in the blood samples, and comparing the content of the compound between the blood samples before and after the administration of the candidate substance, wherein the compound is selected from the group consisting of phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA, isoleucine, hydroxyproline and cystathionine.

(28) A diagnostic method for diagnosing depression, the method including the step of measuring a content of one or more compounds in the blood sample of a subject to be tested, wherein the compound is selected from the group consisting of ADP-RIBOSE, ATP, ADP, AMP, serotonin, tryptophan, kynurenine, SDMA(symmetric dimethylarginine), threonine, glyceric acid, serine, N-acetylaspartic acid, glutamic acid, trigonelline, creatine, 2-methyl serine, sphingosine, homovanillic acid, piperidine, sulfoxidated methionine, pipecolic acid, sphinganine, γ-butyrobetaine, guanidoacetic acid, isobutyric acid, creatinine, sarcosine, 3-methyl butyric acid, nicotinamide, betaine, ornithine, carnitine, ethanolamine, phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA (asymmetric dimethylarginine), isoleucine, hydroxyproline and cystathionine.

(29) The diagnostic method according to Item (28), the method including the step of measuring a content of one or more compounds in the blood sample of the subject, wherein the compound is selected from the group consisting of phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA, isoleucine, hydroxyproline and cystathionine.

(30) The diagnostic method according to Item (28), the method including the steps of:

measuring a content of a first compound selected from the group consisting of hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA, isoleucine, hydroxyproline and cystathionine in the blood sample of the subject, and measuring a content of a second compound selected from the group consisting of phosphoethanolamine and taurine in the blood sample of the subject.

(31) The diagnostic method according to Item (28), the method including the step of measuring a content of aspartic acid and arginine in the blood sample of the subject.

(32) The diagnostic method according to Item (28), the method including the step of measuring a content of aspartic acid and tyrosine in the blood sample of the subject.

(33) The diagnostic method according to Item (28), the method including the step of measuring a content of tyrosine and glucaric acid in the blood sample of the subject.

(34) The diagnostic method according to Item (28), the method including the step of measuring a content of tyrosine and 3-aminobutyric acid in the blood sample of the subject.

(35) A diagnostic method for diagnosing severity of depression, the method including the step of measuring a content of cystathionine in blood sample of a patient.

(36) The diagnostic method for diagnosing depression according to Item (28), the method including the step of measuring a content of one or more compounds in the blood sample of the subject to be tested, wherein the compound is selected from the group consisting of ADMA (asymmetric dimethylarginine), hypotaurine, lysine, histidine, leucine, β-alanine, choline, threonine, glyceric acid, isocitric acid, serine, malic acid, 2-methyl serine, sphingosine, homovanillic acid, sulfoxidated methionine, sphinganine, phenylalanine, alanine, aminoadipic acid, N-acetylaspartic acid, glutamic acid, trigonelline, creatine, guanidoacetic acid, isobutyric acid, creatinine, sarcosine, betaine, phosphoethanolamine, taurine, ADP-RIBOSE, aspartic acid, tyrosine, ATP, ADP, asparagine, AMP, serotonin, valine, tryptophan, kynurenine, phosphorylcholine, isoleucine, SDMA (symmetric dimethylarginine), piperidine, pipecolic acid, creatine and nicotinamide.

(37) The diagnostic method for diagnosing depression according to Item (28), the method including the step of measuring a content of one or more compounds in the blood sample of the subject, wherein the compound is selected from the group consisting of phosphoethanolamine, taurine, ADP-RIBOSE, aspartic acid, tyrosine, ATP, ADP, asparagine, AMP, serotonin, valine, tryptophan, kynurenine, phosphorylcholine, isoleucine, SDMA, piperidine, pipecolic acid, creatinine and nicotinamide.

(38) The diagnostic method for diagnosing depression according to Item (28), the method including the step of measuring a content of one or more compounds in the blood sample of the subject, wherein the compound is selected from the group consisting of ADMA, hypotaurine, lysine, histidine, leucine, β-alanine, choline, threonine, glyceric acid, isocitric acid, serine, malic acid, 2-methyl serine, sphingosine, homovanillic acid, sulfoxidated methionine, sphinganine and isobutyric acid.

(39) The diagnostic method for diagnosing depression according to Item (28), the method including the step of measuring a content of one or more compounds in the blood sample of the subject, wherein the compound is selected from the group consisting of phenylalanine, alanine, aminoadipic acid, N-acetylaspartic acid, glutamic acid, trigonelline, creatine, guanidoacetic acid, sarcosine and betaine.

(40) A program to cause a computer to execute the steps of:

obtaining a content of a biomarker in a blood sample collected from a subject to be tested, making a judgement based on the content as to whether the subject is either one or more of a healthy subject, not a healthy subject, a patient with depression and/or not a patient with depression, and outputting the result of the judgement, wherein the biomarker is selected from the group consisting of ADP-RIBOSE, ATP, ADP, AMP, serotonin, tryptophan, kynurenine, SDMA(symmetric dimethylarginine), threonine, glyceric acid, serine, N-acetylaspartic acid, glutamic acid, trigonelline, creatine, 2-methyl serine, sphingosine, homovanillic acid, piperidine, sulfoxidated methionine, pipecolic acid, sphinganine, γ-butyrobetaine, guanidoacetic acid, isobutyric acid, creatinine, sarcosine, 3-methyl butyric acid, nicotinamide, betaine, ornithine, carnitine, ethanolamine, phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA (asymmetric dimethylarginine), isoleucine, hydroxyproline and cystathionine.

(41) The program according to Item (40), further including the step of causing an apparatus for measuring biomarker to measure the content of the biomarker in the blood sample.

(42) A recording medium readable by a computer, the medium storing the program according to Item (40) or (41).

(43) The method according to any one of Items (19) to (22), wherein the depression is atypical depression.

(44) The method according to Item (23) or (24), wherein the plurality of patients diagnosed as being afflicted with depression include a patient diagnosed as being afflicted with atypical depression.

(45) The method according to Item (26) or (27), wherein the patient with depression is a patient afflicted with atypical depression.

DESCRIPTION OF EMBODIMENTS

Hereinafter the embodiments of the present invention accomplished based on the abovementioned findings are described in detail with reference to Examples. Note that the objective, characteristics, and advantages of the present invention as well as the idea thereof will be apparent to those skilled in the art from the descriptions given herein, and the present invention can be easily worked by a person skilled in the art based on these descriptions. It is to be understood that the embodiments and specific examples of the invention described hereinbelow are to be taken as preferred examples of the present invention. These embodiments and examples are presented only for illustrative or explanatory purposes, and are not intended to restrict the present invention thereto. It is apparent to those skilled in the art that various changes and modifications may be made based on the descriptions given herein within the intent and scope of the present invention disclosed herein.

==Depression to be Diagnosed Using Biomarker==

As used herein, the "biomarkers for diagnosing depression" (hereinafter the term "biomarker for diagnosing" is also referred to as "diagnostic marker") include the biomarkers that can identify patients with depression with high probability (disease markers), as well as the biomarkers that can exclude healthy subjects from the patients with depression with high probability (health markers).

==Method for Measuring Content of Diagnostic Marker==

The diagnostic marker according to the present invention may be phosphoethanolamine, taurine, hypotaurine, aspartic acid, methionine, tyrosine, phosphorylcholine, arginine, asparagine, 3-aminobutyric acid, β-alanine, phenylalanine, lysine, phosphocreatine, alanine, uric acid, choline, isocitric acid, leucine, malic acid, aminoadipic acid, tyramine, valine, glucaric acid, histidine, ADMA (asymmetric dimethylarginine), isoleucine, hydroxyproline or cystathionine. Whether or not a patient is afflicted with depression may be diagnosed by measuring a content of the diagnostic marker in a blood sample collected from the patient.

When the content of the diagnostic marker in the collected blood sample is to be measured, the blood sample may be preferably pretreated prior to the measurement. For example, a serum or plasma can be separated from the blood by incubation or centrifugation, and the separated serum or plasma may be preferably subjected to the measurement.

The content of a compound as the diagnostic marker in the collected blood sample may be measured by any known method. Examples of such method include, but not limited to, analysis of the mass of a target compound following isolation, such as high-performance liquid chromatography-mass spectrometer (LC-MS) and gas chromatography-mass spectrometer (GC-MS). When high-performance liquid chromatography is to be employed, any of those columns (ex. ion-exchange columns) capable of simultaneously analyzing multiple ionic metabolites may be preferably used.

Other methods for measuring the target compound include, but not limited to, those of measurement employing NMR analysis, those of measurement employing acid-base neutralization titration, those of measurement employing amino acid analyzer, those of measurement with enzymes, those of measurement using nucleic acid aptamars/peptide aptamers, those of measurement employing colorimetry, those of measurement only with high-performance liquid chromatography, those of measurement only with gas chromatography, and those of measurement only with mass spectrometer. When the high-performance liquid chromatography is to be employed, any of those columns (ex. ion-exchange columns) capable of simultaneously analyzing multiple ionic metabolites may be preferably used.

Use of capillary electrophoresis-time-of-flight mass spectrometer (CE-TOFMS) for the measurement is preferable in that it is capable of simultaneously analyzing the in-blood contents of all of the multiple compounds as the diagnostic markers. When CE-TOFMS is to be employed for the measurement, the pretreated serum or plasma may be further pretreated, preferably as follows.

The serum or plasma is mixed with an alcoholic solvent to terminate enzymatic reactions remaining in the serum or plasma. A preferable alcoholic solvent is methanol. The terminated serum or plasma is mixed with an organic solvent and water, and the mixture is subjected to phase separation and the organic phase containing liposoluble materials such as phospholipids etc. is removed. The organic solvent to be used may be of any type that can be separated from water by phase separation, and preferable examples are dichloromethane, chloroform, dichloroethane etc., and chloroform is particularly preferable. It is preferable that proteins are removed from the aqueous phase thus obtained. The method to remove proteins may be preferably ultrafiltration but not limited thereto. After removal of proteins, the alcoholic solvent remaining in the aqueous phase is preferably removed by distillation. The distillation methods for removal of the solvent include, but not limited to, natural drying, vacuum drying and centrifugal vacuum drying, but the centrifugal vacuum drying is preferable in that it can be conducted quickly and conveniently. Thus an aqueous solution can be prepared from the collected blood sample by removing insoluble materials, and this aqueous solution from which insoluble materials are removed may be preferably subjected to a measurement using CE-TOFMS.

The samples to be subjected to measurement with CE-TOFMS may also include an internal standard to provide criteria for measurements of electrophoresis time, content, etc. of compounds as the diagnostic marker. The internal standard can be any compound that does not interfere with the efficiency of electrophoresis or mass spectroscopy, and preferable examples include methionine sulfone and 10-camphor sulfonate (10-camphorsulfonic acid, CSA).

The capillary to be used in the capillary electrophoresis is preferably made of fused-silica. The internal diameter of the capillary is preferably no more than 100 µm to ensure better separation, and is most preferably 50 µm. The length of the capillary is preferably in the range of 50 cm to 150 cm.

Fractions containing the compound as the target diagnostic marker among those obtained by the capillary electrophoresis may be identified by any method, and examples include a method in which the electrophoretic migration time of the target compound is measured using a sample of the compound in advance, as well as a method in which relative values of the migration time are compared with that of an internal standard.

As the content of the compound as the target diagnostic marker, the peak area at the m/z of the target compound in the fraction identified to contain the compound is then measured. Each peak area can be normalized by comparing it with the peak area of the internal standard. The absolute concentration of the compound as the diagnostic marker in the collected blood sample can be calculated from the measured peak area by making a calibration curve using a sample of the target compound. The calibration curve is made preferably by the standard addition method rather than the standard solution method.

==Use of Diagnostic Marker==

The diagnostic marker can be used in various embodiments of the present invention, including those illustrated below.

<Method for Diagnosing Depression>

First, a blood sample is collected from a human or non-human vertebrate. The collected blood sample may be used for diagnosing a disease by measuring the content of a diagnostic marker in the blood (hereinafter also referred to as a marker level). The in-blood content of a biomarker is preferably the absolute concentration of the biomarker, but may be any value that is correlated with the absolute concentration of the biomarker and can be used for comparison of the absolute concentrations among individuals, and examples include the relative concentration, the weight per unit volume, and the raw data from the measurement of absolute concentrations (for example, the value obtained by normalizing the peak area in a graph from CE-TOFMS measurement).

Prior to the diagnosis, measured are the ranges of the in-blood biomarker levels of individuals in a vertebrate species having been diagnosed as being afflicted with depression (hereinafter referred to as diseased individuals) and individuals in a vertebrate species having been diagnosed as not having depression (hereinafter referred to as healthy individuals). If a biomarker level in a blood sample of a subject vertebrate falls within the range of the in-blood biomarker level for the healthy vertebrate, then the probability that this vertebrate has not been afflicted with the disease is high, whereas if it falls within the range of the in-blood biomarker level for the diseased vertebrate, then the probability that the animal has been afflicted with disease is high. The diseased vertebrate may have had atypical depression. The diseased vertebrate as well as the subject vertebrate may also be complicated with another disease such as anxiety disorder, borderline personality disorder or panic disorder.

The range of in-blood biomarker level of the healthy vertebrate may be obtained by measuring in advance the range of in-blood biomarker levels of a subject of a vertebrate species at a time when the same vertebrate was healthy, and this range of biomarker level in the healthy state can be used when making diagnosis using the marker level at that time of the diagnosis.

The range of the in-blood biomarker level of the healthy vertebrate may be any range of values appropriate for diagnosing a disease by using a diagnostic marker, and it may be a range between an average plus a standard deviation and the average minus the standard deviation, or a range from the lower limit to the upper limit of the average, in which the average can be obtained from multiple measurements on each animal. The most preferable value or range for each diagnostic marker may be chosen for the diagnosis.

Alternatively, a threshold for the in-blood biomarker level may be determined to distinguish diseased individuals of a vertebrate species from healthy individuals of the vertebrate species. For example, in-blood biomarker levels of plurality of diseased individuals and plurality of healthy individuals may be measured to determine the threshold in advance. The threshold may be determined by any method known to those skilled in the art. For example, a threshold can be determined so that diseased individuals are included below the threshold (or above the threshold) at a first predetermined ratio and healthy individuals are included above the threshold (or below the threshold) at a second predetermined ratio. In an exemplary method, a statistical software such as JMP from SAS Inc. can be used to obtain a threshold value with which chi-square test yields the best result. A diagnostic marker is preferably provided with high values of both the first predetermined ratio and the second predetermined ratio; for example, the value may be no less than 70%, more preferably no less than 80%, even more preferably no less than 90%, and most preferably 100%. When both values are set high, specificity as well as sensitivity can be high. If it is impossible to set both of the first and second predetermined ratios high, the threshold may be determined so that either one of the specificity and the sensitivity becomes high. The values of both the specificity and sensitivity are high; for example, the value may be no less than 70%, more preferably no less than 80%, even more preferably no less than 90%, and most preferably 100%. As used herein, the specificity refers to a percentage value of (the number of healthy individuals above or below the threshold)/(the total number of healthy individuals), and the sensitivity refers to a percentage value of (the number of diseased individuals below or above the threshold)/(the total number of diseased individuals). Biomarkers having a high specificity can be suitably used as the biomarker for identifying a patient with depression (hereinafter referred to as a disease marker) because the probability of a patient being afflicted with depression is high if the level of such a biomarker of the patient is below (or above) the threshold. Biomarker having high sensitivity can be suitably used as the biomarker for excluding a healthy subject from patients with depression (hereinafter referred to as a health marker) because probability of a patient not being afflicted with depression is high if the level of such a biomarker is above (or below) the threshold.

The diagnostic markers according to the present invention may be used as a disease marker as well as a health marker. Among them, phosphoethanolamine, taurine, aspartic acid, methionine, tyrosine, aminoadipic acid, histidine, isoleucine, ADP-RIBOSE, tyrosine, ATP, ADP, asparagine, AMP, serotonin, valine, tryptophan, kynurenine, phosphorylcholine, SDMA (symmetric dimethylarginine), piperidine, pipecolic acid, creatinine, and nicotinamide are effective as both of the disease marker and the health marker, and their plasma concentration in a subject vertebrate may be measured to make a diagnosis that the probability of the subject being either afflicted with depression or healthy is high if the concentration falls in such a certain range as illustrated in Table 1 for human subjects. Among the biomarkers, asparagine, phenylalanine, glucaric acid, hydroxyproline, cystathionine, alanine, aminoadipic acid, N-acetylaspartic acid, glutamic acid, trigonelline, creatine, guanidoacetic acid, sarcosine and betaine are suitably used as the disease markers, and their plasma concentration in a subject vertebrate may be measured to make a diagnosis that the probability of the subject being afflicted with depression is high if the concentration falls in such a certain range as illustrated in Table 1 for human subjects. Further, hypotaurine, phosphorylcholine, arginine, 3-aminobutyric acid, β-alanine, lysine, phosphocreatine, alanine, uric acid, choline, isocitric acid, leucine, malic acid, tyramine, valine, ADMA (asymmetric dimethylarginine), threonine, glyceric acid, serine, 2-methyl serine, sphingosine, homovanillic acid, sulfoxidated methionine, sphinganine, isobutyric acid are suitably used as the health markers, and their plasma concentration in a subject vertebrate may be measured to make a diagnosis that the probability of the subject being healthy is high if the concentration falls in such a certain range as illustrated for human subjects in either Table 1 derived from Example 1 or Table 2 derived from Example 2. When phosphoethanolamine or taurine is to be used as the biomarker, the threshold may be preferably set to 2.41 or 50.54 (μM) respectively. The thresholds described herein are merely examples calculated from a particular population by a particular method, and they are likely to vary for different population.

TABLE 1

| Biomarker | Threshold (μM) | Depressive (Above or below) | Healthy |
| --- | --- | --- | --- |
| Phosphoethanolamine | 1.99 | Below | Above |
| Taurine | 44.47 | Below | Above |
| Hypotaurine | 2.15 | Below | Above |
| Aspartic acid | 3.95 | Below | Above |
| Methionine | 20.33 | Below | Above |
| Tyrosine | 67.19 | Below | Above |
| Phosphocholine | 0.87 | Below | Above |
| Arginine | 89.27 | Below | Above |
| Asparagine | 36.26 | Below | Above |
| 3-aminobutyric acid | 11.50 | Above | Below |
| β-alanine | 4.47 | Below | Above |
| Phenylalanine | 43.27 | Below | Above |
| Lysine | 193.52 | Below | Above |
| Phosphocreatine | 0.93 | Above | Below |
| Alanine | 446.47 | Below | Above |
| Uric acid | 332.05 | Below | Above |
| Choline | 28.84 | Below | Above |
| Isocitric acid | 6.90 | Below | Above |
| Leucine | 188.26 | Below | Above |
| Malic acid | 2.08 | Below | Above |
| 2-aminoadipic acid | 0.70 | Below | Above |
| Tyramine | 0.23 | Above | Below |
| Valine | 251.05 | Below | Above |
| Glucaric acid | 0.42 | Above | Below |
| ADMA | 0.33 | Below | Above |
| Histidine | 76.35 | Below | Above |
| Isoleucine | 30.59 | Below | Above |
| Hydroxyproline | 8.81 | Below | Above |
| Cystathionine | 5.63 | Above | Below |

TABLE 2

| Biomarker | Threshold (μM) | Depressive (Above or below) | Healthy |
| --- | --- | --- | --- |
| Phosphoethanolamine | 2.06 | Below | Above |
| Taurine | 44.20 | Below | Above |
| ADP-ribose | 0.11 | Below | Above |
| Aspartic acid | 2.88 | Below | Above |
| Tyrosine | 66.85 | Below | Above |
| ATP | 1.76 | Below | Above |
| Methionine | 20.12 | Below | Above |
| ADMA | 0.33 | Below | Above |
| Hypotaurine | 2.15 | Below | Above |
| ADP | 0.93 | Below | Above |
| Lysine | 193.49 | Below | Above |
| Phenylalanine | 43.27 | Below | Above |
| Asparagine | 36.58 | Below | Above |
| AMP | 0.48 | Below | Above |
| Serotonin | 0.11 | Below | Above |
| Histidine | 90.39 | Below | Above |
| Valine | 223.95 | Below | Above |
| Leucine | 187.94 | Below | Above |
| Alanine | 362.35 | Below | Above |
| Tryptophan | 48.66 | Below | Above |
| β-alanine | 3.29 | Below | Above |
| Aminoadipic acid | 0.41 | Below | Above |
| Kynurenine | 1.17 | Below | Above |
| Phosphorylcholine | 0.59 | Below | Above |
| Isoleucine | 30.59 | Below | Above |
| SDMA | 0.42 | Below | Above |
| Choline | 28.84 | Below | Above |
| Threonine | 120.64 | Below | Above |
| Glyceric acid | 16.89 | Below | Above |
| Isocitric acid | 6.90 | Below | Above |
| Serine | 128.87 | Below | Above |
| N-acetylaspartic acid | 0.23 | Below | Above |
| Malic acid | 2.08 | Below | Above |
| Glutamic acid | 20.05 | Below | Above |
| Trigonelline | 0.18 | Below | Above |
| Creatine | 0.55 | Below | Above |
| 2-methyl serine | 16.65 | Below | Above |
| Sphingosine | 13.38 | Below | Above |
| Homovanillic acid | 2.65 | Below | Above |
| Piperidine | 0.04 | Below | Above |
| Sulfoxidated methionine | 3.64 | Below | Above |
| Pipecolic acid | 1.10 | Below | Above |
| Sphinganine | 56605.00 | Below | Above |
| γ-butyrobetaine | 2.72 | Below | Above |
| Uric acid | 332.05 | Below | Above |
| Guanidoacetic acid | 2.03 | Below | Above |
| Isobutyric acid | 2.40 | Below | Above |
| Creatinine | 60.58 | Below | Above |
| Sarcosine | 2.68 | Below | Above |
| 3-methyl butyric acid | 0.62 | Below | Above |
| Nicotinamide | 0.26 | Below | Above |
| Betaine | 26.13 | Below | Above |
| 3-aminobutyric acid | 12.24 | Above | Below |
| Ornithine | 90.34 | Below | Above |
| Carnitine | 43.03 | Below | Above |
| Ethanolamine | 11.11 | Below | Above |

These biomarkers may be used in combination to improve accuracy of diagnosis, and they may be combined in any combination. For example, when two kinds of disease markers are used, if only one of them is at a concentration indicating the probability of depression, then the subject may still be diagnosed as being afflicted with depression at a certain probability, but if both of the markers are at concentrations indicating the probability of depression, then the probability of depression would be higher than that in the case of the one marker. In a preferred embodiment, a health marker is used in combination with a disease marker. For example, a subject of an animal individual is diagnosed using a health marker, and if the health marker is at a concentration indicating a state of "not being healthy", then the subject is further diagnosed by using a disease marker. If the disease marker is at a concentration indicating a state of "being afflicted", then the probability of being afflicted with depression is judged to be high, whereas if the disease marker is not at a concentration indicating the state of "being afflicted", then the probability of being healthy is judged to be high. In this way, the accuracy of diagnosis can be made higher than the case where only disease marker is used. When the health marker is at a concentration indicating a state of "being healthy", the subject may be diagnosed as being probably healthy, but when another diagnosis is made using a disease marker and if it is at a concentration indicating a state of "not being afflicted", then the probability of being healthy would be even higher. If the disease marker is at a concentration indicating a state of "being afflicted", then further diagnosis may be made, for example, by analyzing the distance of the concentration of the biomarkers from their respective thresholds, or judgement by using a third biomarker.

When identifying subjects with depression using plurality of biomarkers, the health marker may be used as a first biomarker with its threshold set at a higher level in order to increase the sensitivity, and subjects with high probability of being healthy may be excluded first. The threshold may be set at any high level, for example at about 90%, preferably at about 92%, and even more preferably at about 94%. According to this method, if the health marker at the first stage is proved to be at a concentration indicating a state of being "healthy", then the subject may be diagnosed as being healthy with high probability. When the health marker is not at the concentration indicating the state of being "healthy", the diagnostic marker may be used in the next step, and if the marker is at a concentration indicating the state of "being afflicted", then the probability of being afflicted with depression is judged to be high, whereas if the marker is not at the concentration indicating the state of "being afflicted", then the probability of being healthy is judged to be high. In this way, the accuracy of the judgement can be improved.

The diagnosis using these diagnostic markers may be combined with another conventional diagnostic method, such as an examination by interview or questionnaire.

The use of the diagnostic markers as described herein not only enables diagnosis with more easiness and higher accuracy at psychiatry, but also provides means for screening at the scenes such as health checkup where precise diagnosis cannot be conducted, clinical departments such as internal medicine and surgery other than psychiatry, and emergency conditions where verbal communication with a patient is not possible. In this way, it becomes possible to bring potential patients with depression who have been left off the psychiatric examination to the psychiatry department that should be the first place where they are to be treated.

By setting the threshold for the sensitivity of a marker at a very high level, the marker can be effectively used as a health marker. The threshold can be set at any high level, for example at about 90%, preferably at about 92%, and even more preferably at about 94%. At the scene of the health checkup where precise diagnosis cannot be conducted, a diagnosis using such a threshold may be employed as a first diagnosis. In this method, a subject who falls in the range which includes only small number of patients with depression but large number of healthy subjects is diagnosed as being healthy, whereas a patient who falls in the range which includes large number of patients with depression is diagnosed as being afflicted with depression at high probability, and then referred to a psychiatry department for specialized diagnosis. In this way, the ratio of patients with depression in the first diagnosis can be increased, thereby reducing the burden of second diagnosis at the psychiatry department.

The depression to be diagnosed herein may be of any type that can be diagnosed by a conventional diagnostic method, and preferable examples are depressions that can be judged according to SCID Interview method. Patients having adjustment disorder are preferably excluded in advance by a conventional diagnostic method such as an examination by interview or questionnaire. Patients having anxiety disorder, personality disorders such as borderline personality disorder and depressive personality disorder or dysthymic disorders can be diagnosed, in which case the use of ADMA, hypotaurine, lysine, histidine, leucine, β-alanine, choline, threonine, glyceric acid, isocitric acid, serine, malic acid, 2-methyl serine, sphingosine, homovanillic acid, sulfoxidated methionine, sphinganine, phenylalanine, alanine, aminoadipic acid, N-acetylaspartic acid, glutamic acid, trigonelline, creatine, guanidoacetic acid, sarcosine, betaine, phosphoethanolamine, taurine, ADP-RIBOSE, aspartic acid, tyrosine, ATP, ADP, asparagine, AMP, serotonin, valine, tryptophan, kynurenine, phosphorylcholine, isoleucine, SDMA, piperidine, pipecolic acid, isobutyric acid, creatinine, nicotinamide and the like are preferable, and the threshold for them are preferably taken from those shown in Table 2, or thresholds obtained by the same method as used for Table 2. Patients not having anxiety disorder, personality disorder such as borderline personality disorder and depressive personality disorder, nor dysthymic disorder can be diagnosed by any of the markers according to the present invention, and the thresholds to be used for them can be taken from both of Table 1 and Table 2, but the thresholds shown in Table 1 or thresholds obtained by the same method as used for Table 1 is more preferable.

<Method for Judging Severity of Depression>

The plasma concentration of cystathionine is inversely proportional to the scale by CESD as well as to the number of diagnostic match with SCID, and therefore cystathionine is useful as a biomarker for judging the severity of depression in a patient with depression.

First, whether or not a subject animal is in depression is judged by using either any of the biomarkers according to the present invention or any conventional diagnostic method such as the examination by interview or questionnaire. Then the plasma concentration of the patient with depression is examined, and if it is, for example, less than 18.36 μM, then a diagnosis of mild depression may be made, whereas if 18.36 μM or more, then diagnosis of severe depression may be made.

<Judgment of Drug Efficacy>

The effect of a therapeutic agent for certain disease often varies for different individuals. Therefore, knowing the efficacy of the therapeutic agent for a certain individual is quite beneficial, and it can be easily achieved by using the diagnostic marker according to the present invention. For example, blood samples are collected from a diseased vertebrate before and after administering a therapeutic agent for depression, and the content of a diagnostic marker in the collected blood samples is measured to make comparison of the content of the diagnostic marker between the blood samples before and after the administration of the therapeutic agent. A judgment for the therapeutic agent as being effective can be made if the content of the diagnostic marker comes closer to the range indicating the state as being healthy after the administration of the therapeutic agent. In this way, the diagnostic marker according to the present invention can be used to easily judge whether a therapeutic agent is effective.

<Method for Screening Model Animal for Depression>

By using the diagnostic marker according to the present invention, model animals with depression can be screened easily. For example, whether a candidate animal (excluding human) is indeed a model animal for depression may be judged by a diagnosis of the candidate animal, in which the content of the diagnostic marker in the blood of the animal is measured and compared with the content of the diagnostic marker in blood of a healthy animal of the same species.

<Method for Screening Drug with Effectiveness for Depression>

By using experimental animal of depression, a compound that has effectiveness for treatment of depression can be identified. For example, a compound as a candidate of a therapeutic agent for depression is administered to a model animal (excluding human) of depression, from which blood samples are collected before and after the administration, and the content of a diagnostic marker in the blood samples is measured to make comparison of the content of the diagnostic marker between the blood samples before and after the administration of the compound. A judgment for the administered compound as being effective for treatment of depression can be made if the content of the diagnostic marker comes closer to the range indicating the state as being healthy after the administration of the compound. In this way, the diagnostic marker according to the present invention can be used to easily screen compounds having effectiveness for treatment of a disease.

<Method for Screening Drug Most Effective for Diseased Animal>

In the case where drugs have different efficacy depending on different individuals, a drug that is most effective for a certain individual with depression can be screened by administering plurality of drugs to the individual and then conducting diagnosis using the diagnostic marker.

==Computer for Utilizing Biomarker==

After the content of a compound as the diagnostic marker in a blood sample collected from an individual of a vertebrate species is measured as described above, the result of the measurement may be transmitted to a computer, and the computer may utilize the results according to any of the methods described herein.

For example, a medical practitioner collects a blood sample from an individual of a vertebrate species and appropriately treats it, then loads the blood sample on an apparatus for measuring the biomarker. The computer causes an apparatus for measuring the biomarker to measure the content of the biomarker in the sample, and obtains the result of the measurement. Based on the plasma content of the marker thus obtained, the computer may then make a judgement as to whether the tested subject is either one or more selected from a group consisting of a healthy subject, not a healthy subject, a patient with depression and not a patient with depression. The computer may also make judgements regarding the severity of a depression, the efficacy of an antidepressant, and the like, similarly to the method described above. The computer may output the result of the judgements thus made, thereby enabling the medical practitioner to obtain information about the tested subject.

It should be noted that the program according to the present invention causes a computer to execute a method to utilize the plasma content of the marker thus obtained. It may also cause a computer to execute the step of causing the biomarker-measuring apparatus to measure the content of the biomarker in the sample.

The program may be recorded on a recording medium which is readable by a computer, and the recording medium may be any of a hard disk, CD, CD, DVD, USB memory, a floppy disk, and the like.

EXAMPLES

Embodiments of the present invention are hereinafter described by referring to examples, but the scope of the present invention is not to be limited to the examples described hereinbelow. In this example, it is demonstrated that patients with depression can be indeed distinguished from healthy subjects by using the marker according to the present invention on the patients who have been preliminary diagnosed as being depressed.

Example 1

[1] Diagnosis of Depressive Patients

Depressive patients were chosen from the outpatients at Hospital of National Center of Neurology and Psychiatry who have been diagnosed as being afflicted with depression by SCID (Structured Clinical Interview for Diagnosis) Interview Method mainly during their first to third examination, and who have agreed to volunteer under a predetermined procedure for informed consent as approved by Ethics Committee. The major depression (MD) that is complicated with disease in Axis I or Axis II was excluded. The SCID Interview Method stands for one type of differentiation diagnoses for psychiatric disorders, and is a structured interview to enable reproducible diagnosis under the DSM-IV criteria. The first-time diagnosis was conducted to obtain general information by questioning with regard to lifestyle including smoking habit, drug usage, chief complaint, menstruation and sleeping conditions as well as medical information such as anamnesis, family history, presence of physical disorders and test results for type-B hepatitis, type-C hepatitis, head CT, blood biochemistry, cardiography and radiographs. After informed consents were obtained, questionnaires were made for CESD (a scale for depression) and STAI (a score for anxiety). Missing answers were checked by conducting a direct interview with a research coordinator (a clinical psychologist). In order to obtain the plasma concentration of the markers according to the present invention, 14 mL of blood sample was collected from each of the patients, and then plasma was separated within 2 hours, and stored in liquid nitrogen until measurement. Excluded were the depressive patients being complicated with any of the anxiety disorders, patients with mild depression that is difficult to differentiate from the adjustment disorders, patients with depression accompanied by borderline personality disorder or any personality disorder, and patients having an episode of major depression during the development of dysthymic disorder, and the remaining Axis I patients and the patients of major depression (MD) having no complication with disease in Axis-II were chosen in the total number of 35 for the analyses.

Meanwhile, healthy subjects were recruited through advertisements etc. at National Institute of Mental Health and chosen from those who offered volunteering. Informed consents were first obtained at a laboratory of National Institute of Mental Health, and then the subjects were tested by questioning with regard to lifestyle including smoking habit, drug usage, chief complaint, menstruation, sleeping conditions, anamnesis, family history, presence of physical disorders, CESD and STAI. Those who scored 21 or more in CESD were excluded as not being healthy subjects only by questionnaire. Also, most of the subjects who turned out by the interview to be under treatment of any physical disorder were excluded. In the questionnaire, missing answers were checked by conducting a direct interview with a research coordinator (a clinical psychologist). The subjects diagnosed as being healthy were thus chosen in the total number of 41. In order to obtain the plasma concentrations of the markers according to the present invention, 14 mL of blood sample was collected from each of the subjects, and plasma was separated within 2 hours, and stored in liquid nitrogen until measurement.

Table 3 shows sexes, ages and results from the psychiatric tests (CESD, STAI) of the depressive patients as well as the healthy subjects.

TABLE 3

| | Sex | Count | Age (SD) | CESD (SD) | STAI-S (SD) | STAI-T (SD) |
|---|---|---|---|---|---|---|
| Depressive group | Male | 15 | 42.1 (16.6) | 27.7 (11.7) | 63.1 (12.8) | 53.5 (6.7) |
| | Female | 20 | 38.0 (13.9) | 33.7 (6.8) | 61.8 (9.5) | 53.5 (9.6) |
| | Total | 35 | 39.7 (14.9) | 30.9 (9.6) | 62.3 (10.8) | 53.5 (8.4) |
| Healthy group | Male | 17 | 45.5 (11.4) | 7.1 (3.9) | 42.1 (5.8) | 52.0 (5.8) |
| | Female | 24 | 30.5 (12.1) | 9.0 (5.9) | 42.3 (7.9) | 50.9 (8.0) |
| | Total | 41 | 36.7 (13.9) | 8.2 (5.2) | 42.3 (7.0) | 51.4 (2.8) |

With regard to the distribution of the sex, a chi-square test showed no difference between the groups of depressive patients and healthy subjects. With regard to the age, a t-test showed no significant difference between the depressive patients and the healthy subjects, or between males or between females in each of the groups. No significant difference was found between both groups with regard to marital status, working status, body height, body weight, weight change in one month prior to the test, or smoking frequency, either.

In the results of CESD scale determined by a self-report in which the state of depressive symptom is represented, a t-test showed a significant difference at $p<0.01$ between the depressive patients and the healthy subjects, as well as a significant difference between males or between females in each of the groups. No significant difference was found between the males and the females in each of the groups. In the results of STAI-S score that represents the state of anxiety at the time of interview by a self-report, a t-test showed a significant difference at $p<0.05$ between the depressive patients and the healthy subjects, as well as a significant difference between males and between females in each of the groups. No significant difference was found between the males and the females in each of the groups. By contrast, in the results of STAI-T score that measures the innate likelihood of a subject to develop anxiety, no significant difference was found between the depressive patients and the healthy subjects, nor between males or between females in each of the groups. No significant difference was found between the males and the females in each of the group, either.

Followings are the psychosocial indexes that showed a significant difference between the two groups. Significantly higher frequency of insomnia symptoms of poor falling asleep and early morning awakening was found in the depressive group. BMI was slightly larger in the depressive group. Frequency for the alcohol intake was slightly higher in the healthy group. With regard to the level of educational status, while the depressive group included larger number of junior high school graduates, the healthy group included postgraduates, showing relatively lower educational status of the depressive group.

Use of medicine at the time of the test yielded a significant difference ($p<0.01$) in the chi-square test as shown in Table 4 below. The medicine taken by healthy subjects were painkillers for headache, backache, etc. and antihypertensives, whereas the medicine taken by the depressive patients was mainly hypnotics and anxiolytics, and SSRI was taken by 7 patients.

TABLE 4

| | Drug usage | | |
|---|---|---|---|
| | Not in use | In use | Total |
| Depressive group | 9 | 26 | 35 |
| Healthy group | 30 | 11 | 41 |
| Total | 38 | 37 | 76 |

[2] Preparation of Plasma Sample

In order to measure the amount in blood of the compound as one of the diagnostic markers by using capillary electrophoresis-time-of-flight mass spectrometer (CE-TOFMS), the plasma samples for CE-TOFMS measurement were prepared in the method described below.

Blood samples were collected from the patients under informed consent (conducted at National Center of Neurology and Psychiatry), and 100 µL each of plasma was prepared and put into a centrifuge tube. As an internal standard solution, 0.45 mL of methanol (Wako Pure Chemical, LC/MS grade) containing 10 µM of methionine sulfone and 10 µM of 10-camphor sulfonate (H3304-1002, purchased from Human Metabolome Technologies, Inc.) was added. After addition of 0.5 mL of chloroform (Wako Pure Chemical, reagent grade) and 200 µL of Milli-Q water, the sample was vigorously mixed by vortex for 30 sec., and centrifuged (4° C., 2300×g, 5 min). The aqueous phase was transferred to a ultrafiltration unit (Millipore, Ultrafree-MCPBCC centrifugal filter unit, 5 kDa) and filtered by centrifugation (4° C., 9100×g, 2 to 4 hours) until almost no solution was remained in the filter cup. After the filter cup was removed, the filtrate was dried by centrifugation under vacuum. The dried material was redissolved in 50 µL of Milli-Q water containing the internal standard to prepare the sample for the measurement by CE-TOFMS.

[3] Method for CE-TOFMS Measurement and Analysis of Result

The CE-TOFMS measurement and the following data analyses were conducted on Agilent CE-TOF-MSD System (Agilent Technologies Inc.) using fused silica capillaries.

The conditions for the CE-TOFMS measurement were as follows:

(A) Cation Mode
   Run buffer: Cation Buffer Solution (p/n: H3301-1001)
   Rinse buffer: Cation Buffer Solution (p/n: H3301-1001)
   Sample injection: Pressure injection 50 mbar, 10 sec
   CE voltage: Positive, 30 kV
   MS ionization: ESI Positive
   MS capillary voltage: 4,000 V
   MS scan range: m/z 50-1,000
   Sheath liquid: HMT Sheath Liquid (p/n: H3301-1020)

(B) Anion Mode
   Run buffer: Anion Buffer Solution (p/n: H3302-1021)
   Rinse buffer: Anion Buffer Solution (p/n: H3302-1022)
   Sample injection: Pressure injection 50 mbar, 25 sec
   CE voltage: Positive, 30 kV
   MS ionization: ESI Negative
   MS capillary voltage: 3,500 V
   MS scan range: m/z 50-1,000
   Sheath liquid: HMT Sheath Liquid (p/n: H3301-1020)

From the peaks detected by CE-TOFMS, m/z values, migration times (MT) and area values were obtained as the peak information. The peak area values obtained were converted to relative area values by Formula 1 below.

$$\text{Relative area} = \frac{\text{Area of target peak}}{\text{Area of internal standard}} \quad \text{[Formula I]}$$

[4] Measurement of Plasma Concentration of Diagnostic Marker by CE-TOFMS and Analysis of Result Blood samples were collected from the depressive patients and the healthy subjects, and the samples for the CE-TOFMS measurement were prepared from the plasma, and subjected to the measurement by CE-TOFMS under cation mode and anion mode. From these measurements, peak areas were obtained as the data representing the content of each compound in each of the samples.

From the data of peak areas, a value that yields the best chi-square value of judgement was chosen using the statistical software JMP from SAS Inc. as the threshold of the disease marker to distinguish depressive patients from healthy subjects. Also, using commercially available samples, a calibration curve was made and used to convert the thresholds thus obtained to absolute values (threshold (μM)) based on the concentration in the plasma. Table 5 shows the thresholds for the disease markers used and the numbers of the healthy subjects and depressive patients fall in the range above or below the thresholds, and the results of the calculation of specificity and sensitivity based on these values are shown in Table 6.

TABLE 5

|  |  | Above | Below |
|---|---|---|---|
| Phosphoethanolamine | Depressive | 3 | 32 |
|  | Healthy | 33 | 8 |
| Taurine | Depressive | 8 | 27 |
|  | Healthy | 35 | 6 |
| Hypotaurine | Depressive | 2 | 33 |
|  | Healthy | 19 | 22 |
| Aspartic acid | Depressive | 1 | 34 |
|  | Healthy | 26 | 15 |
| Methionine | Depressive | 6 | 29 |
|  | Healthy | 28 | 13 |
| Tyrosine | Depressive | 1 | 34 |
|  | Healthy | 25 | 16 |
| Phosphocholine | Depressive | 0 | 35 |
|  | Healthy | 12 | 29 |
| Arginine | Depressive | 1 | 34 |
|  | Healthy | 17 | 24 |

TABLE 5-continued

|  |  | Above | Below |
|---|---|---|---|
| Aspartic acid | Depressive | 16 | 19 |
|  | Healthy | 34 | 7 |
| 3-aminobutyric acid | Depressive | 33 | 2 |
|  | Healthy | 24 | 17 |
| β-alanine | Depressive | 1 | 34 |
|  | Healthy | 13 | 28 |
| Phenylalanine | Depressive | 21 | 14 |
|  | Healthy | 39 | 2 |
| Lysine | Depressive | 3 | 32 |
|  | Healthy | 21 | 20 |
| Phosphocreatine | Depressive | 35 | 0 |
|  | Healthy | 32 | 9 |
| Alanine | Depressive | 1 | 34 |
|  | Healthy | 13 | 28 |
| Uric acid | Depressive | 0 | 35 |
|  | Healthy | 12 | 29 |
| Choline | Depressive | 3 | 32 |
|  | Healthy | 17 | 24 |
| Isocitric acid | Depressive | 1 | 34 |
|  | Healthy | 13 | 28 |
| Leucine | Depressive | 1 | 34 |
|  | Healthy | 16 | 25 |
| Malic acid | Depressive | 1 | 34 |
|  | Healthy | 13 | 28 |
| Aminoadipic acid | Depressive | 7 | 28 |
|  | Healthy | 25 | 16 |
| Tyramine | Depressive | 35 | 0 |
|  | Healthy | 36 | 5 |
| Valine | Depressive | 5 | 30 |
|  | Healthy | 22 | 19 |
| Glucaric acid | Depressive | 6 | 29 |
|  | Healthy | 0 | 41 |
| ADMA | Depressive | 0 | 35 |
|  | Healthy | 12 | 29 |
| Histidine | Depressive | 11 | 24 |
|  | Healthy | 31 | 10 |
| Isoleucine | Depressive | 7 | 28 |
|  | Healthy | 25 | 16 |
| Hydroxyproline | Depressive | 17 | 18 |
|  | Healthy | 28 | 13 |
| Cystathionine | Depressive | 34 | 1 |
|  | Healthy | 34 | 7 |

TABLE 6

|  | Performance when used a sole marker | | | | Depressive | Healthy |
|---|---|---|---|---|---|---|
|  | Specificity | Sensitivity | Threshold | Threshold (μM) | (Above or below) | |
| Phosphoethanolamine | 80.5% | 91.4% | 0.0059 | 1.99 | Below | Above |
| Taurine | 85.4% | 77.1% | 0.1133 | 44.47 | Below | Above |
| Hypotaurine | 46.3% | 94.3% | 0.0113 | 2.15 | Below | Above |
| Aspartic acid | 63.4% | 97.1% | 0.0316 | 3.95 | Below | Above |
| Methionine | 68.3% | 82.9% | 0.2743 | 20.33 | Below | Above |
| Tyrosine | 61.0% | 97.1% | 0.8549 | 67.19 | Below | Above |
| Phosphocholine | 29.3% | 100.0% | 0.0099 | 0.87 | Below | Above |
| Arginine | 41.5% | 97.1% | 1.6627 | 89.27 | Below | Above |
| Asparagine | 82.9% | 54.3% | 0.4149 | 36.26 | Below | Above |
| 3-aminobutyric acid | 41.5% | 94.3% | 0.0038 | 11.50 | Above | Below |
| β-alanine | 31.7% | 97.1% | 0.0398 | 4.47 | Below | Above |
| Phenylalanine | 95.1% | 40.0% | 1.0038 | 43.27 | Below | Above |
| Lysine | 51.2% | 91.4% | 2.5304 | 193.52 | Below | Above |
| Phosphocreatine | 22.0% | 100.0% | 0.0022 | 0.93 | Above | Below |
| Alanine | 31.7% | 97.1% | 4.6678 | 446.47 | Below | Above |
| Uric acid | 29.3% | 100.0% | 1.1712 | 332.05 | Below | Above |
| Choline | 41.5% | 91.4% | 0.5004 | 28.84 | Below | Above |
| Isocitric acid | 31.7% | 97.1% | 0.0462 | 6.90 | Below | Above |
| Leucine | 39.0% | 97.1% | 3.7470 | 188.26 | Below | Above |
| Malic acid | 31.7% | 97.1% | 0.0456 | 2.08 | Below | Above |
| 2-aminoadipic acid | 61.0% | 80.0% | 0.0097 | 0.70 | Below | Above |
| Tyramine | 12.2% | 100.0% | 0.0034 | 0.23 | Above | Below |
| Valine | 53.7% | 85.7% | 4.5583 | 251.05 | Below | Above |
| Glucaric acid | 100.0% | 17.1% | 0.0021 | 0.42 | Above | Below |
| ADMA | 29.3% | 100.0% | 0.00113 | 0.33 | Below | Above |

TABLE 6-continued

| | Performance when used a sole marker | | | | Depressive | Healthy |
|---|---|---|---|---|---|---|
| | Specificity | Sensitivity | Threshold | Threshold (μM) | (Above or below) | |
| Histidine | 75.6% | 68.6% | 1.2351 | 76.35 | Below | Above |
| Isoleucine | 61.0% | 80.0% | 1.7544 | 30.59 | Below | Above |
| Hydroxyproline | 68.3% | 51.4% | 0.0849 | 8.81 | Below | Above |
| Cystathionine | 97.1% | 17.1% | 0.0008 | 5.63 | Above | Below |

Among the compounds listed, hypotaurine, phosphorylcholine, arginine, 3-aminobutyric acid, β-alanine, lysine, phosphocreatine, alanine, uric acid, choline, isocitric acid, leucine, malic acid, tyramine, valine, ADMA (asymmetric dimethylarginine) etc. have particularly high sensitivity, indicating their potential for excluding healthy subjects, and therefore they can be preferably used as health markers. Meanwhile, asparagine, phenylalanine, glucaric acid, hydroxyproline, cystathionine etc. have particularly high specificity, indicating their potential for finding patients, and therefore they can be preferably used as disease markers. In particular, the compounds having both the sensitivity and specificity over 60%, i.e. phosphoethanolamine, taurine, aspartic acid, methionine, tyrosine, aminoadipic acid, histidine, isoleucine etc. are useful as both the disease marker and the health marker, and each one of them may be used solely for diagnosis.

Since the contents of these compounds in blood can be easily measured all at once by simply analyzing a blood sample by CE-TOFMS, the results from plurality of these compounds can be quite easily combined to make diagnosis.

[5] Use of Health Marker for Effectively Excluding Healthy Subject

In this example, the abovementioned compounds were used as biomarkers wherein the threshold for their sensitivity as health markers was set to 94.3%. The numbers of depressive patients or healthy subjects included in the ranges above the threshold or below the threshold are shown in Table 7, and the results of the calculation for their specificity are shown in Table 8.

TABLE 7

| Marker | | Above | Below |
|---|---|---|---|
| Aspartic acid | Depressive | 2 | 33 |
| | Healthy | 28 | 13 |
| Methionine | Depressive | 2 | 33 |
| | Healthy | 19 | 22 |
| Tyrosine | Depressive | 2 | 33 |
| | Healthy | 26 | 15 |
| Phosphocholine | Depressive | 2 | 33 |
| | Healthy | 16 | 25 |
| Arginine | Depressive | 2 | 33 |
| | Healthy | 17 | 24 |
| Asparagine | Depressive | 2 | 33 |
| | Healthy | 13 | 28 |
| 3-aminobutyric acid | Depressive | 33 | 2 |
| | Healthy | 24 | 17 |
| β-alanine | Depressive | 2 | 33 |
| | Healthy | 13 | 28 |
| Phenylalanine | Depressive | 2 | 33 |
| | Healthy | 15 | 26 |
| Lysine | Depressive | 2 | 33 |
| | Healthy | 13 | 28 |
| Phosphocreatine | Depressive | 33 | 2 |
| | Healthy | 26 | 15 |
| Alanine | Depressive | 2 | 33 |
| | Healthy | 13 | 28 |
| Uric acid | Depressive | 2 | 33 |
| | Healthy | 13 | 28 |

TABLE 7-continued

| Marker | | Above | Below |
|---|---|---|---|
| Choline | Depressive | 2 | 33 |
| | Healthy | 13 | 28 |
| Isocitric acid | Depressive | 2 | 33 |
| | Healthy | 13 | 28 |
| Leucine | Depressive | 2 | 33 |
| | Healthy | 17 | 24 |
| Malic acid | Depressive | 2 | 33 |
| | Healthy | 14 | 27 |
| 2-aminoadipic acid | Depressive | 2 | 33 |
| | Healthy | 8 | 33 |
| Tyramine | Depressive | 33 | 2 |
| | Healthy | 33 | 8 |
| Valine | Depressive | 2 | 33 |
| | Healthy | 12 | 28 |
| Glucaric acid | Depressive | 33 | 2 |
| | Healthy | 33 | 8 |
| ADMA | Depressive | 2 | 33 |
| | Healthy | 15 | 26 |
| Histidine | Depressive | 2 | 33 |
| | Healthy | 16 | 25 |
| Isoleucine | Depressive | 2 | 33 |
| | Healthy | 16 | 25 |

TABLE 8

| | Specificity when sensitivity is set to 94.3% | | | |
|---|---|---|---|---|
| | Specificity | Sensitivity | Threshold | Threshold (um) |
| Aspartic acid | 68.3% | 94.3% | 0.0306 | 3.832 |
| Methionine | 46.3% | 94.3% | 0.2986 | 22.134 |
| Tyrosine | 63.4% | 94.3% | 0.8506 | 66.854 |
| Phosphocholine | 39.0% | 94.3% | 0.0087 | 0.761 |
| Arginine | 41.5% | 94.3% | 1.6627 | 89.272 |
| Asparagine | 31.7% | 94.3% | 0.5623 | 49.144 |
| 3-aminobutyric acid | 41.5% | 94.3% | 0.0038 | 11.625 |
| β-alanine | 31.7% | 94.3% | 0.0398 | 4.469 |
| Phenylalanine | 36.6% | 94.3% | 1.4551 | 62.729 |
| Lysine | 31.7% | 94.3% | 2.8313 | 216.536 |
| Phosphocreatine | 36.6% | 94.3% | 0.0026 | 1.105 |
| Alanine | 31.7% | 94.3% | 4.6678 | 446.472 |
| Uric acid | 31.7% | 94.3% | 1.1507 | 326.248 |
| Choline | 31.7% | 94.3% | 0.5303 | 30.565 |
| Isocitric acid | 31.7% | 94.3% | 0.0462 | 6.899 |
| Leucine | 41.5% | 94.3% | 3.5795 | 179.846 |
| Malic acid | 34.1% | 94.3% | 0.0431 | 1.965 |
| Aminoadipic acid | 19.5% | 94.3% | 0.0144 | 0.702 |
| Tyramine | 19.5% | 94.3% | 0.0036 | 0.242 |
| Valine | 29.3% | 94.3% | 5.1873 | 285.691 |
| Glucaric acid | 19.5% | 94.3% | 0.0006 | 0.128 |
| ADMA | 39.0% | 94.3% | 0.0106 | 0.305 |
| Histidine | 36.6% | 94.3% | 1.4057 | 86.896 |
| Isoleucine | 39.0% | 94.3% | 2.1169 | 36.914 |

Determination of a threshold in this way makes it possible to seclude depressive patients to a range either above or below the threshold. Thus, the ratio of depressive patients among total subjects can be increased by adopting a range that contains a larger number of depressive patients.

Practically, in the case where the sensitivity is set to 94.3%, as long as the specificity is 5.7 (=100−94.3) % or higher, this method can increase the ratio of depressive patients in a population regardless of the ratios of depressive patients and healthy subjects. All of the biomarkers listed in Table 8 have specificity of 5.7% or higher, and therefore are useful as the health markers.

[6] Diagnosis Using Plurality of Biomarkers

The accuracy of diagnosis can be improved by using plurality of biomarkers among the abovementioned compounds. Effective combinations are considered to be, in particular, the combination of a disease marker and a health marker, the combination of a biomarker effective for both and a disease marker, the combination of a biomarker effective for both and a health marker, and the combination of two biomarkers effective for both. Their specific examples areas follows:

(1) Where the patients with aspartic acid less than 3.95 µM and arginine less than 89.27 µM are defined as depressive and the others are defined as healthy, the sensitivity is 94% and the specificity is 88%.
(2) Where the patients with aspartic acid less than 3.95 µM and tyrosine less than 67.19 µM are defined as depressive and the others are defined as healthy, the sensitivity is 94% and the specificity is 81%.
(3) Where the patients with tyrosine less than 67.19 µM and glucaric acid 0.42 µM or more are defined as depressive and the others are defined as healthy, the sensitivity is 94% and the specificity is 81%.
(4) Where the patients with tyrosine less than 67.19 µM and 3-aminobutyric acid less than 11.50 µM are defined as depressive and the others are defined as healthy, the sensitivity is 91% and the specificity is 85%.

Thus, the accuracy of diagnosis is improved in comparison to the case where each of the biomarkers is used alone.

[7] Biomarker for Judging Severity of Depression

Similar to Example 4, the content of cystathionine in each sample from the depressive patient group was obtained in the form of peak area data, and was tested by Spearman's rank correlation coefficient in relation to the CESD scale as well as the number of diagnostic matches in SCID. Inverse correlation was found with CESD by $r=-0.460$ and $p=0.039$, and with SCID by $r=-0.339$ and $p=0.049$.

Then, the threshold of the cystathionine content between mildly depressive patients and severely depressive patients was analyzed, and it was found that the mildly depressive patients and severely depressive patients could be distinguished at the threshold of 0.00265 as shown in Table 9. In this example, those who scored 30 or less in CESD were defined as being afflicted with mild depression, whereas those of 31 or higher were defined as severe depression, and those who matched 5 to 6 items out of the 9 criteria in SCID were defined as mild depression, whereas those of 7 or more matches were defined as severe depression.

TABLE 9

|  | Above | Below |
|---|---|---|
| CESD - mild | 4 | 14 |
| CESD - severe | 13 | 4 |
| SCID - mild | 5 | 13 |
| SCID - severe | 8 | 9 |

Thus, cystathionine can be effectively used as a diagnostic marker for depression, in particular, the biomarker for judging the severity of depression.

It should be noted that the threshold could be converted to an absolute concentration of about 18.36 µM.

Example 2

[1] Diagnosis of Depressive Patients

In this example, the analyses were conducted on the patient group consisting of 34 Axis I patients including 3 depressive patients complicated with anxiety disorders other than adjustment disorder and 2 depressive patients complicated with borderline personality disorder, as well as the control group including 7 patients with mild depression which was difficult to distinguish from adjustment disorder, and 31 healthy subjects. The subjects in the patient group and the control group were chosen in the similar way to Example 1. Between both groups, no significant difference was found in terms of age, body height, body weight, BMI and sex. There was no significant difference in marital status, working status, weight change in one month prior to the test, or smoking frequency, either.

[2] Methods for Preparation of Plasma Sample, Measurement by CE-TOFMS and Analysis of Result The methods for preparation of plasma samples from the abovementioned subjects to be tested and the measurement of each marker in the samples by CE-TOFMS were the same as those in Example 1.

[3] Measurement of Plasma Concentration of Diagnostic Marker by CE-TOFMS and Analysis of Result The measurement of the concentration of diagnostic markers in the plasma of the subjects from the patient group and the control group, determination of the thresholds, and the analyses of the results were conducted in the similar way to Example 1.

Table 10 shows the results of the analyses for each of the diagnostic markers.

TABLE 10

| | | | Below threshold | | Above threshold | | | |
|---|---|---|---|---|---|---|---|---|
| Biomarker | Threshold | Threshold (concentration) | Depression patient | Healthy subject | Depression patient | Healthy subject | Sensitivity | Specificity |
| Phosphoethanolamine | 0.0061 | 2.06 | 28 | 2 | 6 | 36 | 82.4% | 94.7% |
| Taurine | 0.1126 | 44.20 | 26 | 4 | 8 | 34 | 76.5% | 89.5% |
| ADP-ribose | 0.0005 | 0.11 | 32 | 11 | 2 | 27 | 94.1% | 71.1% |
| Aspartic acid | 0.023 | 2.88 | 21 | 3 | 13 | 35 | 61.8% | 92.1% |
| Tyrosine | 0.8506 | 66.85 | 33 | 13 | 1 | 25 | 97.1% | 65.8% |
| ATP | 0.0063 | 1.76 | 28 | 6 | 6 | 32 | 82.4% | 84.2% |
| Methionine | 0.2714 | 20.12 | 29 | 13 | 5 | 25 | 85.3% | 65.8% |
| ADMA | 0.0113 | 0.33 | 34 | 24 | 0 | 14 | 100.0% | 36.8% |

TABLE 10-continued

| Biomarker | Threshold | Threshold (concentration) | Below threshold Depression patient | Below threshold Healthy subject | Above threshold Depression patient | Above threshold Healthy subject | Sensitivity | Specificity |
|---|---|---|---|---|---|---|---|---|
| Hypotaurine | 0.0113 | 2.15 | 33 | 16 | 1 | 22 | 97.1% | 57.9% |
| ADP | 0.0049 | 0.93 | 28 | 8 | 6 | 30 | 82.4% | 78.9% |
| Lysine | 2.53 | 193.49 | 30 | 16 | 4 | 22 | 88.2% | 57.9% |
| Phenylalanine | 1.0038 | 43.27 | 14 | 1 | 20 | 37 | 41.2% | 97.4% |
| Asparagine | 0.4186 | 36.58 | 21 | 5 | 13 | 33 | 61.8% | 86.8% |
| AMP | 0.0019 | 0.48 | 30 | 14 | 4 | 24 | 88.2% | 63.2% |
| Serotonin | 0.0016 | 0.11 | 22 | 5 | 12 | 33 | 64.7% | 86.8% |
| Histidine | 1.4623 | 90.39 | 34 | 27 | 0 | 11 | 100.0% | 28.9% |
| Valine | 4.0663 | 223.95 | 21 | 6 | 13 | 32 | 61.8% | 84.2% |
| Leucine | 3.7406 | 187.94 | 32 | 21 | 2 | 17 | 94.1% | 44.7% |
| Alanine | 3.7883 | 362.35 | 19 | 6 | 15 | 32 | 55.9% | 84.2% |
| Tryptophan | 0.9408 | 48.66 | 26 | 11 | 8 | 27 | 76.5% | 71.1% |
| β-alanine | 0.0293 | 3.29 | 30 | 17 | 4 | 21 | 88.2% | 55.3% |
| Aminoadipic acid | 0.0057 | 0.41 | 9 | 0 | 25 | 38 | 26.5% | 100.0% |
| Kynurenine | 0.0256 | 1.17 | 31 | 15 | 3 | 23 | 91.2% | 60.5% |
| Phosphorylcholine | 0.0067 | 0.59 | 24 | 11 | 10 | 27 | 70.6% | 71.1% |
| Isoleucine | 1.7544 | 30.59 | 27 | 14 | 7 | 24 | 79.4% | 63.2% |
| SDMA | 0.01 | 0.42 | 25 | 12 | 9 | 26 | 73.5% | 68.4% |
| Choline | 0.5004 | 28.84 | 31 | 21 | 3 | 17 | 91.2% | 44.7% |
| Threonine | 1.9038 | 120.64 | 34 | 28 | 0 | 10 | 100.0% | 26.3% |
| Glyceric acid | 0.0473 | 16.89 | 31 | 19 | 3 | 19 | 91.2% | 50.0% |
| Isocitric acid | 0.0462 | 6.90 | 32 | 22 | 2 | 16 | 94.1% | 42.1% |
| Serine | 1.0526 | 128.87 | 29 | 17 | 5 | 21 | 85.3% | 55.3% |
| N-acetylaspartic acid | 0.0012 | 0.23 | 12 | 2 | 22 | 36 | 35.3% | 94.7% |
| Malic acid | 0.0456 | 2.08 | 32 | 22 | 2 | 16 | 94.1% | 42.1% |
| Glutamic acid | 0.2428 | 20.05 | 13 | 3 | 21 | 35 | 38.2% | 92.1% |
| Trigonelline | 0.0034 | 0.18 | 12 | 1 | 22 | 37 | 35.3% | 97.4% |
| Creatine | 0.193 | 0.55 | 7 | 0 | 27 | 38 | 20.6% | 100.0% |
| 2-methyl serine | 0.2012 | 16.65 | 29 | 21 | 5 | 17 | 85.3% | 44.7% |
| Sphingosine | 13.3825 | 13.38 | 28 | 16 | 6 | 22 | 82.4% | 57.9% |
| Homovanillic acid | 0.0109 | 2.65 | 34 | 32 | 0 | 6 | 100.0% | 15.8% |
| Piperidine | 0.0006 | 0.04 | 23 | 10 | 11 | 28 | 67.6% | 73.7% |
| Sulfoxidated methionine | 0.0216 | 3.64 | 34 | 30 | 0 | 8 | 100.0% | 21.1% |
| Pipecolic acid | 0.0263 | 1.10 | 22 | 13 | 12 | 25 | 64.7% | 65.8% |
| Sphinganine | 56605 | 56605.00 | 28 | 16 | 6 | 22 | 82.4% | 57.9% |
| γ-butyrobetaine | 0.0671 | 2.72 | 34 | 30 | 0 | 8 | 100.0% | 21.1% |
| Uric acid | 1.1712 | 332.05 | 34 | 26 | 0 | 12 | 100.0% | 31.6% |
| Guanidoacetic acid | 0.0264 | 2.03 | 14 | 4 | 20 | 34 | 41.2% | 89.5% |
| Isobutyric acid | 0.0517 | 2.40 | 28 | 20 | 6 | 18 | 82.4% | 47.4% |
| Creatinine | 0.9358 | 60.58 | 24 | 15 | 10 | 23 | 70.6% | 60.5% |
| Sarcosine | 0.0304 | 2.68 | 16 | 6 | 18 | 32 | 47.1% | 84.2% |
| 3-methyl butyric acid | 0.0472 | 0.62 | 29 | 20 | 5 | 18 | 85.3% | 47.4% |
| Nicotinamide | 0.0024 | 0.26 | 25 | 15 | 9 | 23 | 73.5% | 60.5% |
| Betaine | 0.6112 | 26.13 | 10 | 2 | 24 | 36 | 29.4% | 94.7% |
| 3-aminobutyric acid | 0.004 | 12.24 | 34 | 30 | 0 | 8 | 100.0% | 21.1% |
| Ornithine | 1.5677 | 90.34 | 32 | 26 | 2 | 12 | 94.1% | 31.6% |
| Carnitine | 1.3303 | 43.03 | 26 | 18 | 8 | 20 | 76.5% | 52.6% |
| Ethanolamine | 0.0492 | 11.11 | 31 | 26 | 3 | 12 | 91.2% | 31.6% |

Among the compounds listed, ADMA, hypotaurine, lysine, histidine, leucine, β-alanine, choline, threonine, glyceric acid, isocitric acid, serine, malic acid, 2-methyl serine, sphingosine, homovanillic acid, sulfoxidated methionine, sphinganine, isobutyric acid etc. have particularly high sensitivity, indicating their potential for excluding healthy subjects, and therefore they can be preferably used as health markers. Meanwhile, phenylalanine, alanine, aminoadipic acid, N-acetylaspartic acid, glutamic acid, trigonelline, creatine, guanidoacetic acid, sarcosine, betaine etc. have particularly high specificity, indicating their potential for identifying patients, and therefore they can be preferably used as disease markers. In particular, the compounds having both the sensitivity and specificity over 60%, i.e. phosphoethanolamine, taurine, ADP-RIBOSE, aspartic acid, tyrosine, ATP, ADP, asparagine, AMP, serotonin, valine, tryptophan, kynurenine, phosphorylcholine, isoleucine, SDMA (symmetric dimethylarginine), piperidine, pipecolic acid, creatinine, nicotinamide etc. are useful as both the disease marker and the health marker, and each one of them may be used solely for diagnosis.

[4] Set of Health Marker and its Threshold for Effectively Excluding Healthy Subject This example demonstrates that health markers can effectively exclude healthy subjects.

When the threshold for each of the biomarkers was set so that their sensitivity becomes 94.1%, an exclusion of the healthy subjects was effectively achieved by excluding a population containing smaller number of depressive patients. The specificity was calculated at the threshold, and the results are shown in Table 11.

TABLE 11

| Biomarker | Threshold | Threshold (concentration) | Below threshold Depression patient | Below threshold Healthy subject | Above threshold Depression patient | Above threshold Healthy subject | Sensitivity | Specificity |
|---|---|---|---|---|---|---|---|---|
| ADP-Ribose | 0.0005 | 0.11 | 2 | 32 | 23 | 15 | 94.1% | 74.2% |
| Tyrosine | 0.8506 | 66.85 | 2 | 32 | 22 | 16 | 94.1% | 71.0% |
| Hypotaurine | 0.0113 | 2.14 | 2 | 32 | 17 | 21 | 94.1% | 54.8% |
| Methionine | 0.3008 | 22.30 | 2 | 32 | 16 | 22 | 94.1% | 51.6% |
| ADMA | 0.0103 | 0.30 | 2 | 32 | 16 | 22 | 94.1% | 51.6% |
| β-Alanine | 0.0334 | 3.75 | 2 | 32 | 15 | 23 | 94.1% | 48.4% |
| Aspartic acid | 0.0354 | 4.42 | 2 | 32 | 15 | 23 | 94.1% | 48.4% |
| Asparagine | 0.5330 | 46.58 | 2 | 32 | 14 | 24 | 94.1% | 45.2% |
| Taurine | 0.1705 | 66.91 | 2 | 32 | 14 | 24 | 94.1% | 45.2% |
| Leucine | 3.7470 | 188.26 | 2 | 32 | 14 | 24 | 94.1% | 45.2% |
| Uric acid | 1.1407 | 323.41 | 2 | 32 | 14 | 24 | 94.1% | 45.2% |
| Serotonin | 0.0050 | 0.34 | 2 | 32 | 13 | 25 | 94.1% | 41.9% |
| Malic acid | 0.0456 | 2.08 | 2 | 32 | 13 | 25 | 94.1% | 41.9% |
| Isocitric acid | 0.0462 | 6.90 | 2 | 32 | 13 | 25 | 94.1% | 41.9% |
| Lysine | 2.8313 | 216.53 | 2 | 32 | 12 | 26 | 94.1% | 38.7% |
| Histidine | 1.4057 | 86.90 | 2 | 32 | 12 | 26 | 94.1% | 38.7% |
| Choline | 0.5303 | 30.56 | 2 | 32 | 12 | 26 | 94.1% | 38.7% |
| Phenylalanine | 1.4551 | 62.72 | 2 | 32 | 12 | 26 | 94.1% | 38.7% |
| Glutamic acid | 0.5787 | 47.79 | 2 | 32 | 12 | 26 | 94.1% | 38.7% |
| Succinic acid | 0.0390 | 8.36 | 2 | 32 | 12 | 26 | 94.1% | 38.7% |
| Alanine | 4.6678 | 446.47 | 2 | 32 | 11 | 27 | 94.1% | 35.5% |
| Phosphoethanolamine | 0.0106 | 3.58 | 2 | 32 | 11 | 27 | 94.1% | 35.5% |
| Phosphorylcholine | 0.0099 | 0.87 | 2 | 32 | 11 | 27 | 94.1% | 35.5% |
| Serine | 1.1198 | 137.10 | 2 | 32 | 11 | 27 | 94.1% | 35.5% |
| Arginine | 1.6627 | 89.27 | 2 | 32 | 11 | 27 | 94.1% | 35.5% |
| Valine | 5.3006 | 291.93 | 2 | 32 | 10 | 28 | 94.1% | 32.3% |
| γ-Butyrobetaine | 0.0652 | 2.64 | 2 | 32 | 10 | 28 | 94.1% | 32.3% |
| Isoleucine | 2.2144 | 38.61 | 2 | 32 | 10 | 28 | 94.1% | 32.3% |
| N-Acetylaspartic acid | 0.0019 | 0.37 | 2 | 32 | 10 | 28 | 94.1% | 32.3% |
| Lactic acid | 13.2742 | 4297.40 | 32 | 2 | 10 | 28 | 94.1% | 32.3% |
| Ornithine | 1.5677 | 90.34 | 2 | 32 | 10 | 28 | 94.1% | 32.3% |
| Sphinganine 1p | 281.4486 | 281.45 | 2 | 32 | 10 | 28 | 94.1% | 32.3% |
| Sphingosine | 1803.3079 | 1803.31 | 2 | 32 | 10 | 28 | 94.1% | 32.3% |
| Sphingosine 1p | 1803.3079 | 1803.31 | 2 | 32 | 10 | 28 | 94.1% | 32.3% |
| Aminoadipic acid | 0.0142 | 1.02 | 2 | 32 | 9 | 29 | 94.1% | 29.0% |
| Phosphocreatine | 0.0026 | 1.11 | 32 | 2 | 8 | 30 | 94.1% | 25.8% |
| Tyramine | 0.0037 | 0.25 | 32 | 2 | 7 | 31 | 94.1% | 22.6% |

Determination of a threshold in this way makes it possible to seclude depressive patients to a range either above or below the threshold. Thus, the ratio of depressive patients among total subjects can be increased by adopting the range which contains a larger number of depressive patients.

Practically, in the case where the sensitivity is set to 94.1%, as long as the specificity is 5.9 (=100−94.1) % or higher, this method can increase the ratio of depressive patients in a population regardless of the ratios of depressive patients and healthy subjects.

All of the biomarkers listed in Table 8 have specificity of 5.7% or higher, and therefore are useful as the health markers. All of the biomarkers listed in Table 11 have specificity of 5.9% or higher, and therefore are useful as the health markers.

Example 3

[1] Calculation of Plasma Marker Concentration Using Standard Addition Method

In Examples 1 and 2, the calibration curve was made from the commercially available samples as the standard solutions and used to convert the obtained thresholds to absolute values (threshold (μM)) based on the plasma concentration (standard solution method). In this example, standard solutions were prepared at a predetermined series of concentrations, and for each of the samples, a series of the solutions added with each of the standard solutions were prepared to make a calibration curve, and then the plasma marker concentration of each of the samples in Example 2 was determined (standard addition method). Using the concentrations thus obtained, thresholds were determined in the similar way to Example 2, and the resulting threshold for phosphoethanolamine and taurine was 2.41 and 50.54 (μM), respectively.

[2] Change in Plasma Marker Concentration Before and After Treatment

Plasma marker concentrations (μM) of phosphoethanolamine and taurine were measured in 2 depressive patients, who were not included in the populations in Examples 1 and 2, before treatment (pre-treatment) and after a diagnosis as remission of the depression by treatment using medicine such as SSRI for about 6 months (post-treatment). The concentrations were determined by the standard addition method.

TABLE 12

| | Phosphoethanolamine | | Taurine | |
|---|---|---|---|---|
| | Before treatment | After treatment | Before treatment | After treatment |
| Patient "A" | 2.0 | 3.5 | 39.0 | 55.4 |
| Patient "B" | 2.2 | 3.8 | 44.6 | 100.1 |

Thus, the plasma marker concentrations of phosphoethanolamine and taurine in both patients increased to a level comparable to that of the healthy subjects after the treatment. By using the thresholds determined in [1] for example, both the Patient A and Patient B can be diagnosed as being afflicted with depression before the treatment, and as being healthy after the treatment, even using either of the markers.

[3] Validation of Threshold I

Plasma marker concentrations in 11 individuals independent of those tested in Examples 1 and 2 (of whom 6 have been definitively diagnosed as being healthy subjects and 5 as patients with depression) were measured in a similar way to [1] above, and diagnosis was made using the thresholds determined in [1].

TABLE 13

| | | Marker diagnosis | |
|---|---|---|---|
| Subject | Definitive diagnosis | Phosphoethanolamine | Taurine |
| 1 | Depression | Depressive | Depressive |
| 2 | Depression | Depressive | Depressive |
| 3 | Depression | Depressive | Depressive |
| 4 | Depression | Depressive | Healthy |
| 5 | Depression | Healthy | Healthy |
| 6 | Healthy | Healthy | Healthy |
| 7 | Healthy | Healthy | Healthy |
| 8 | Healthy | Healthy | Healthy |
| 9 | Healthy | Healthy | Healthy |
| 10 | Healthy | Healthy | Healthy |
| 11 | Healthy | Healthy | Healthy |

Using the thresholds determined in [1], an appropriate diagnosis could be made for the healthy subjects with a probability of 100%. An appropriate diagnosis could be made for the patients with depression with a probability of 80% when using phosphoethanolamine, and with a probability of 60% when using taurine. Therefore, phosphoethanolamine and taurine are useful as the diagnostic markers of depression.

[4] Validation of Threshold II

Plasma marker concentrations in 14 individuals independent of those tested in Examples 1 to 3 (All have panic disorder. Of them, 9 individuals have been definitively diagnosed as not being patients with depression [marked as healthy subjects in the table], and 5 as being patients of atypical depression) were measured in a similar way to [1] above, and diagnosis was made using the thresholds determined in [1].

TABLE 14

| | | Marker diagnosis | |
|---|---|---|---|
| Subject | Definitive diagnosis | Phosphoethanolamine | Taurine |
| 1 | Atypical depression | Depressive | Depressive |
| 2 | Atypical depression | Depressive | Depressive |
| 3 | Atypical depression | Depressive | Depressive |
| 4 | Atypical depression | Depressive | Healthy |
| 5 | Atypical depression | Depressive | Healthy |
| 6 | Healthy | Healthy | Depressive |
| 7 | Healthy | Healthy | Healthy |
| 8 | Healthy | Healthy | Healthy |
| 9 | Healthy | Healthy | Healthy |
| 10 | Healthy | Healthy | Healthy |
| 11 | Healthy | Healthy | Healthy |
| 12 | Healthy | Healthy | Healthy |
| 13 | Healthy | Healthy | Healthy |
| 14 | Healthy | Healthy | Healthy |

Using the thresholds determined in [1], an appropriate diagnosis could be made for both the depressive patients and non-depressive patients with a probability of 100% when using phosphoethanolamine. In the case of taurine, an appropriate diagnosis could be made for depressive patients with a probability of 60% and non-depressive patients with a probability of 89%. Therefore, phosphoethanolamine and taurine are useful as diagnostic markers of depression for the patients with atypical depression as well. Further, the markers according to the present invention can be used even if depression is complicated with other disease (for example, panic disorder).

[Industrial Applicability]

The present invention can provide the biomarkers for diagnosing depression and the diagnostic methods using the biomarkers.

What is claimed is:

1. A method for diagnosing depression using a biomarker, comprising the steps of:

measuring a level of phosphoethanolamine in a blood sample collected from a subject;

comparing the level of phosphoethanolamine in the blood sample with a predetermined threshold to diagnose that if the level of phosphoethanolamine in the blood sample is below the threshold, the subject is afflicted with depression, wherein the threshold is no greater than 2.41μM; and conducting an examination of the subject by interview or questionnaire to provide another diagnosis by a physician or psychologist of whether the subject is afflicted with depression.

2. The method for diagnosing depression using a biomarker according to claim 1, wherein the measurement of a content level of phosphoethanolamine is conducted by the use of capillary electrophoresis-time-of-flight mass spectrometer, measurement with enzymes or high-performance liquid chromatography.

3. The method for diagnosing depression using a biomarker according to claim 1, wherein the subject is a patient suspected of depression or mild depression which is difficult to distinguish from adjustment disorder, and the threshold is no greater than 2.06μM.

4. The method for diagnosing depression using a biomarker according to claim 3, wherein the measurement of a content level of phosphoethanolamine is conducted by the use of capillary electrophoresis-time-of-flight mass spectrometer, measurement with enzymes or high-performance liquid chromatography.

5. The method for diagnosing depression using a biomarker according to claim 1, wherein the subject is a patient suspected of depression or anxiety disorder.

6. The method for diagnosing depression using a biomarker according to claim 5, wherein the measurement of a content level of phosphoethanolamine is conducted by the use of capillary electrophoresis-time-of-flight mass spectrometer, measurement with enzymes or high-performance liquid chromatography.

7. The method for diagnosing depression using a biomarker according to claim 5, wherein the anxiety disorder is panic disorder.

8. A method for diagnosing a remission of depression by a treatment, comprising the steps of:

measuring a level of phosphoethanolamine in a blood sample collected from a subject, wherein the subject is a patient afflicted with depression before the treatment or a patient with the remission by the treatment;

comparing the level of phosphoethanolamine in the blood sample with a predetermined threshold, wherein the threshold is no greater than 2.41μM and the subject is determined to be in remission of depression when the level of phosphoethanolamine in the blood sample is above the predetermined threshold; and conducting an examination of the subject by interview or questionnaire to provide another determination by a physician or psychologist of whether the subject is in remission of depression.

9. The method of claim 8, further comprising:
administering a treatment to the subject suffering from depression; and
modifying the treatment for the subject in response to the level of phosphoethanolamine in the blood sample being above the predetermined threshold.

10. The method of claim 8, wherein the measurement of a content level of phosphoethanolamine is conducted by the use of capillary electrophoresis-time-of-flight mass spectrometer, measurement with enzymes or high-performance liquid chromatography.

11. The method of claim 1, further comprising:
in response to the level of phosphoethanolamine in the blood sample being below the predetermined threshold, administering a treatment for depression to the subject.

12. The method of claim 1, wherein the measurement of a content level of phosphoethanolamine is conducted by the use of capillary electrophoresis-time-of-flight mass spectrometer, measurement with enzymes or high-performance liquid chromatography.

* * * * *